United States Patent [19]
Takei

[11] Patent Number: 5,757,428
[45] Date of Patent: May 26, 1998

[54] ELECTRONIC EQUIPMENT HAVING VIEWPOINT DETECTION APPARATUS WITH DETERMINATION OF ABNORMAL OPERATION OF EYEBALL ILLUMINATION UNIT

[75] Inventor: Hirofumi Takei, Yokohama, Japan

[73] Assignee: Canon Kabushiki Kaisha, Tokyo, Japan

[21] Appl. No.: 490,138

[22] Filed: Jun. 14, 1995

[30] Foreign Application Priority Data

Jun. 17, 1994 [JP] Japan .................. 6-159397

[51] Int. Cl.$^6$ ................................ H04N 5/225
[52] U.S. Cl. ............................ 348/333; 396/51
[58] Field of Search ...................... 348/333, 334, 348/207; 396/51

[56] References Cited

U.S. PATENT DOCUMENTS

| | | | |
|---|---|---|---|
| 4,486,080 | 12/1984 | Itoh et al. | 396/51 |
| 5,436,679 | 7/1995 | Ohtsuka et al. | 351/206 |
| 5,436,690 | 7/1995 | Watanabe | 396/122 |
| 5,491,532 | 2/1996 | Suzuki et al. | 396/51 |
| 5,570,156 | 10/1996 | Arai et al. | 348/334 |
| 5,579,079 | 11/1996 | Yamada et al. | 396/51 |

FOREIGN PATENT DOCUMENTS

| | | | |
|---|---|---|---|
| 0589857 | 3/1994 | European Pat. Off. | A61B 3/107 |
| 0596749 | 5/1994 | European Pat. Off. | A61B 3/107 |
| 4240583 | 6/1993 | Germany | A61B 3/10 |
| 1241511 | 9/1989 | Japan . | |
| 2-32312 | 2/1990 | Japan . | |

*Primary Examiner*—Wendy Garber
*Attorney, Agent, or Firm*—Fitzpatrick, Cella, Harper & Scinto

[57] ABSTRACT

Abnormality determination of eyeball illumination is performed by a computer on the basis of the output level, i.e., lightness of a cornea reflection image. When an abnormality is determined, a display indicating it is made and a warning is given. At the same time, power supply for eyeball illumination is stopped. The abnormality determination of eyeball illumination is performed by comparing the output level of a cornea reflection image with a predetermined reference value or comparing the output level ratio or difference of the cornea reflection image with a predetermined reference value.

30 Claims, 14 Drawing Sheets

ELECTRONIC EQUIPMENT HAVING VIEWPOINT DETECTION APPARATUS WITH DETERMINATION OF ABNORMAL OPERATION OF EYEBALL ILLUMINATION UNIT

BACKGROUND OF THE INVENTION

1. Field of the Invention

The present invention relates to a viewpoint detection apparatus and electronic equipment having a viewpoint detection apparatus.

2. Related Background Art

In various types of electronic equipment, operation means, input means, and selection means which are based on detection of the viewpoint of a user have recently been proposed to improve operability, input means, and the like.

For example, viewpoint detection is quite effective for an apparatus, such as a video camera, which requires a user to perform various types of operations, input, and selection while continuing photographing of an object image.

Some video cameras have a so-called viewpoint input function of allowing a user to select a marker indicating execution of, e.g., a zooming or fading function with his/her viewpoint so as to execute the selected function, or matching distance measurement area with the viewpoint on a viewfinder screen.

The principle of a viewpoint detection apparatus for executing this viewpoint input function will be described below.

FIGS. 1A (top view) and 1B (side view) show the principle of a viewpoint detection method.

Referring to FIGS. 1A and 1B, light sources 1206a and 1206b are light-emitting diodes (IREDs) or the like, which irradiate infrared light to which an observer is insensitive. The respective light sources are arranged to be almost symmetrical in the x-direction (horizontal direction) about the optical axis of an imaging lens 1211 (see FIG. 1A) and located slightly therebelow in the y-direction (vertical direction) (see FIG. 1B). These light sources illuminate an eyeball of the observer with divergent light. Some light components of the illumination light reflected by the eyeball are focused on an image sensor 1212 via the imaging lens 1211. FIG. 2A is a schematic view showing an eyeball image projected on the image sensor 1212. FIG. 2B is a graph showing the output intensity of the image sensor 1212.

The viewpoint detection method will be described below with reference to the respective drawings. Consider a horizontal plane first. Referring to FIG. 1A, a cornea 1210 of an eyeball 1208 of the observer is illuminated with infrared light irradiated from the light source 1206b. In this case, a cornea reflection image d (virtual image) formed by the infrared light reflected by the surface of the cornea 1210 is focused by the imaging lens 1211 and formed at a position d' on the image sensor 1212. Similarly, the cornea 1210 of the eyeball is illuminated with infrared light irradiated from the light source 1206a. In this case, a cornea reflection image e (virtual image) formed by the infrared light reflected by the cornea 1210 is focused by the imaging lens 1211 and formed at a position e' on the image sensor 1212.

Light beams from edges a and b of a pupil 1301 surrounded by an iris 1204 respectively form images of the edges a and b at positions a' and b' on the image sensor 1212 via the imaging lens 1211. Assume that the rotational angle, θ, of the optical axis of the eyeball 1208 with respect to the optical axis of the imaging lens 1211 is small. In this case, if the x-coordinates of the edges a and b of the pupil 1301 are respectively represented by xa and xb, many x-coordinates xa and xb can be obtained on the image sensor 1212 (see the marks "x" in FIG. 2A). Therefore, first of all, the cornea center, xc, is calculated by the least squares method of circle or the like. Let xo be the x-coordinate of the center of curvature of the cornea 1210, o. Then the rotational angle, θx, with respect to the optical axis of the eyeball 1208 is given by $$oc * \sin\theta x = xc - xo \quad (1)$$

In consideration of a predetermined correction value δx for the middle point, k, between the cornea reflection images d and e, the x-coordinate xo is calculated as follows:

$$xk = (xd + xe)/2 \quad (2)$$

$$xo = (xd + xe)/2 + \delta x \quad (3)$$

where δx is a numerical value geometrically obtained from the method of installing the apparatus, the eyeball distance, and the like (a description of this calculation method will be omitted). A substitution of equation (1) into equation (2) yields $$\theta x = \arcsin[[xc - \{(xd + xe)/2 + \delta x\}]/oc] \quad (4)$$

The rotational angle θx is then rewritten with "'" (apostrophe) being attached to the coordinate of each feature point projected on the image sensor 1212, as follows:

$$\theta x = \arcsin[[xc' - \{(xd' + xe')/2 + \delta x'\}]/oc/\beta] \quad (5)$$

where β is the magnification determined by the distance, sze, from the eyeball 1208 to the imaging lens 1211. In practice, this magnification β is obtained as a function of the distance |xd'−xe'| between cornea reflection images.

Consider a vertical plane next. FIG. 1B shows the corresponding arrangement. Assume that cornea reflection images formed by the two light sources (IREDs) 1206a and 1206b appear at the same vertical position, and the corresponding coordinate is represented by yi. The rotational angle, θy, of the eyeball 1208 is calculated by almost the same method as that used for the case of the horizontal plane except for equation (2). Let yo be the y-coordinate of a center o of curvature. Then it follows that $$yo = yi + \delta y \quad (6)$$

where δy is a numerical value geometrically obtained from the method of installing the apparatus, the eyeball distance, and the like (this calculation method will be omitted). Therefore, the rotational angle θy in the vertical direction is given by $$\theta y = \arcsin[[yc' - (yi' + \delta y')]/oc/\beta] \quad (7)$$

where yc' is the coordinate of the pupil center on the image sensor 1212 in the vertical direction.

The position coordinates (xn, yn) on the viewfinder screen of the video camera on the horizontal and vertical planes are respectively given, using a constant m determined by the viewfinder optical system, as follows:

$$xn = m^* \arcsin\{[xc' - \{(xd' + xe')/2 + \delta x'\}]/oc/\beta\} \quad (8)$$

$$yn = m^* \arcsin\{[yc' - \{(yi' + \delta y')\}]/oc/\beta\} \quad (9)$$

As is apparent from FIGS. 2A to 2C, pupil edges are detected by using the leading edge (xb') and trailing edge (xa') of an output waveform from the image sensor 1212. In addition, the coordinates of a cornea reflection image area are obtained by using steep leading edge portions (xe' and xd').

A function of performing focus adjustment with a viewpoint will be described next. FIG. 3 is a schematic view showing a video camera having a viewpoint focus adjustment function.

The video camera shown in FIG. 3 comprises a lens-image pickup system 101 having a zoom lens and designed to image an object to be photographed, an electronic viewfinder 103 having a viewfinder screen 102 and used to observe the object to be imaged by the lens-image pickup system 101, an objective lens 104 arranged in front of the electronic viewfinder 103, a viewpoint detection unit 106 for detecting the viewpoint of an eye 105 of a photographer, a display circuit 107 for displaying, on the viewfinder screen 102, an AF frame indicating the outline of a focus area and information required for a photographer, e.g., a tape counter and a photography mode, and a system controller 108 for controlling the respective units of this camera.

The viewpoint detection unit 106 comprises an infrared-emitting diode 160 for irradiating infrared light on the eye 105 of the photographer, a dichroic mirror 161 for transmitting visible light and reflecting infrared light, a focusing lens 162 for focusing the infrared light reflected by the dichroic mirror 161, an image pickup element (photoelectric conversion element such as a CCD) 163 for converting the infrared light focused by the focusing lens 162 into an electrical signal, and a viewpoint detection circuit 164 for obtaining the viewpoint of the photographer on the viewfinder screen 102 on the basis of an image of the eye 105 of the photographer on the image pickup element 163.

Since the dichroic mirror 161 transmits visible light, the photographer can observe the viewfinder screen 102 through the objective lens 104. In addition, since the dichroic mirror 161 reflects infrared light, the reflection image irradiated from the infrared-emitting diode 160 onto the eye 105 is reflected. The reflected reflection image of the eye 105 is focused by the focusing lens 162 and formed on the image pickup element 163.

FIG. 4 is a schematic view showing the arrangement of the viewpoint detection circuit 164. The viewpoint detection circuit 164 is mainly constituted by a microcomputer 21 and incorporates a memory 22, an A/D converter 23, a D/A converter 24, and a CPU 25. The CPU 25 transfers infrared light control signals to an infrared light irradiation unit (not shown) including the infrared-emitting diode 160 via the D/A converter 24 to control the infrared light turning-on timing and the amount of infrared light to be emitted.

The CPU 25 outputs a photoelectric conversion element control signal for controlling the photoelectric conversion element 163. A video signal representing an image of the eye 105 of the photographer which is formed on the photoelectric conversion element 163 upon irradiation of the infrared light is A/D-converted by the A/D converter 23, and the resultant data is stored in the internal memory 22. The viewpoint of the photographer on the viewfinder screen 102 is then obtained on the basis of the stored video signal data according to the above-described principle or an algorithm disclosed in, e.g., Japanese Laid-Open Patent Application Nos. 1-241511 and 2-32312.

FIG. 5 is a flow chart briefly showing a processing sequence employed by the CPU 25 in the microcomputer 21 constituting the viewpoint detection circuit 164.

The CPU 25 outputs a photoelectric conversion element activation signal (step S1601), and an IRED turning-on signal (step S1602). The CPU 25 waits until infrared light is irradiated on the eye 105 of the photographer and a reflection image is formed on the photoelectric conversion element 163 (step S1603). The CPU 25 then outputs an IRED turning-off signal (step S1604). The CPU 25 reads out a video signal representing the eye 105 of the photographer from the photoelectric conversion element 163 (step S1605), A/D-converts the signal with the A/D converter 23, and stores the resultant data in the memory 22 (step S1606).

Subsequently, the CPU 25 outputs a photoelectric conversion element deactivation signal (step S1607), and performs viewpoint operation processing on the basis of the video signal representing the eye 105 of the photographer which is stored in the internal memory 22 to obtain the viewpoint of the photographer on the viewfinder screen 102 (step S1608). The viewpoint data is output to the system controller 108 (step S1609). The CPU 25 then checks whether to continue viewpoint detection (step S1610). If viewpoint detection is to be continued, the flow returns to step S1601. Otherwise, the flow returns to step S1610 to check again whether to continue viewpoint detection. Note that the system controller 108 drives the lens-image pickup system 101 on the basis of the viewpoint data to control the focus of the camera on the viewpoint of the photographer or execute the zooming function, the fading function, or the like with a viewpoint switch.

In this conventional arrangement, however, if an eye of the photographer cannot be normally illuminated owing to a failure in the infrared-emitting diode 160 or the like, correct viewpoint information cannot be obtained because the above cornea reflection images are not normally formed.

Assume that the light-emitting diode 1206a in FIG. 1A emits light which is darker than normal light. In this case, as indicated by the output intensity characteristics of the image sensor in FIG. 2C, the leading edge corresponding to a pupil edge portion Xb'1 becomes small. As a result, the microcomputer cannot determine this portion as a pupil edge. For this reason, the viewpoint of the photographer cannot be accurately detected. As a result, the camera is focused on a point different from the viewpoint of the photographer, or the zooming function, the fading function, or the like is erroneously executed with a viewpoint switch different from the viewpoint switch desired by the photographer.

Furthermore, since an infrared-emitting diode (IRED) for emitting light to which the human eye is insensitive is used as a means for illuminating an eye of the photographer, the illumination state of the IRED cannot be checked with the naked eye of the photographer.

SUMMARY OF THE INVENTION

The present invention has been made in consideration of the above situation, and has as its first object to automatically determine an abnormality in an eyeball illumination means in viewpoint detection.

It is the second object of the present invention to automatically determine an abnormality in an eyeball illumination means in viewpoint detection and take proper measures.

In order to achieve the first object, according to a preferred embodiment of the present invention, there is provided a viewpoint detection apparatus including viewpoint detection means for detecting a viewpoint by using a cornea reflection image corresponding to light irradiated on an eyeball by the eyeball illumination means, comprising lightness detection means for detecting a lightness of the cornea reflection image, and abnormality determination means for determining an abnormality in the eyeball illumination means on the basis of the lightness of the cornea reflection image detected by the lightness detection means.

In order to achieve the second embodiment, according to another preferred embodiment of the present invention, there is provided a viewpoint detection apparatus including viewpoint detection means for detecting a viewpoint by using a cornea reflection image corresponding to light irradiated on an eyeball by the eyeball illumination means, comprising lightness detection means for detecting a lightness of the cornea reflection image, abnormality determination means for determining an abnormality in the eyeball illumination means on the basis of the lightness of the cornea reflection image detected by the lightness detection means, and power supply stopping means for stopping power supply to the eyeball illumination means when the abnormality determination means determines that the eyeball illumination means is abnormal.

In order to achieve the second embodiment, according to another preferred embodiment of the present invention, there is provided a viewpoint detection apparatus including viewpoint detection means for detecting a viewpoint by using a cornea reflection image corresponding to light irradiated on an eyeball by the eyeball illumination means, comprising lightness detection means for detecting a lightness of the cornea reflection image, abnormality determination means for determining an abnormality in the eyeball illumination means on the basis of the lightness of the cornea reflection image detected by the lightness detection means, warning means for warning of an abnormality when the abnormality determination means determines that the eyeball illumination means is abnormal.

It is the third object of the present invention to provide a video camera which stops an operation and displays a warning immediately after an abnormality is detected in a viewpoint detection apparatus.

It is the fourth object of the present invention to provide a viewpoint detection apparatus which can perform high-precision detection on the basis of a cornea reflection image.

The above and other objects, features, and advantages of the present invention will be apparent from the following detailed description in conjunction with the accompanying drawings and the appended claims.

DETAILED DESCRIPTION OF THE PREFERRED EMBODIMENTS

Embodiments of the present invention will be described below with reference to the accompanying drawings. Since the principle of viewpoint detection is the same as that in the prior art, a description thereof will be omitted.

Figure 1A:
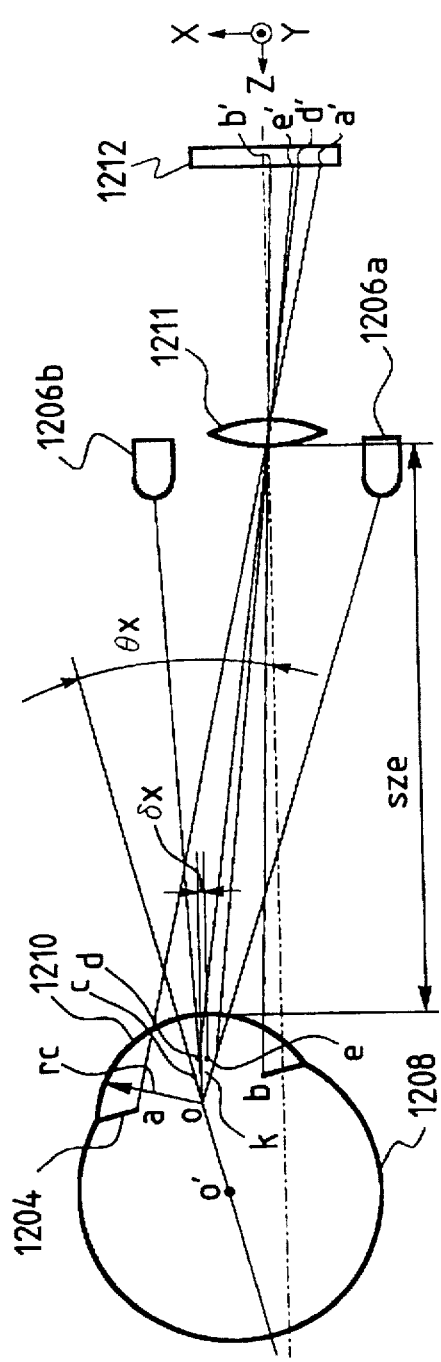
FIGS. 1A and 1B are views for explaining the principle of viewpoint detection.
Figure 1B:
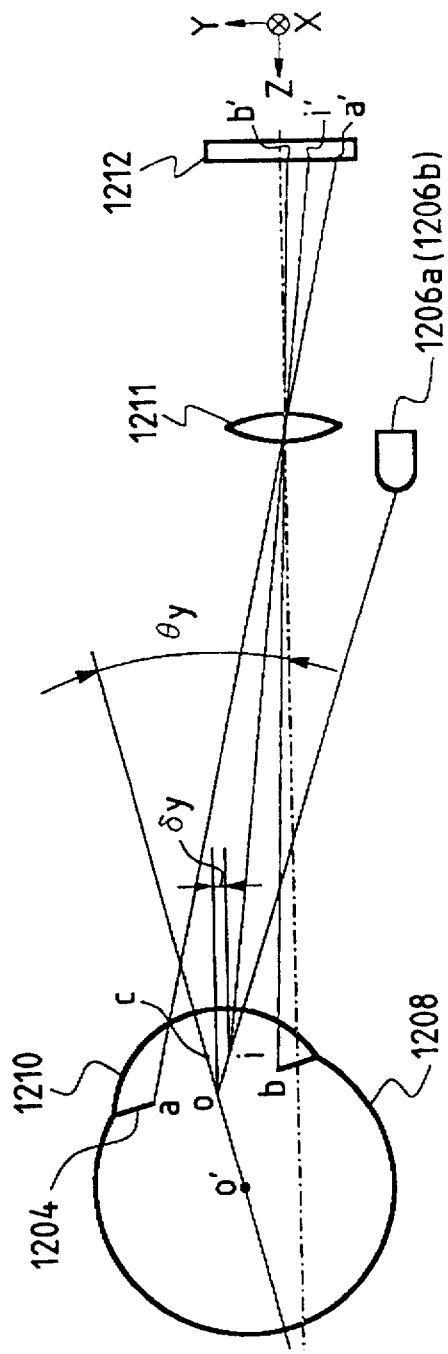
Figure 2A:
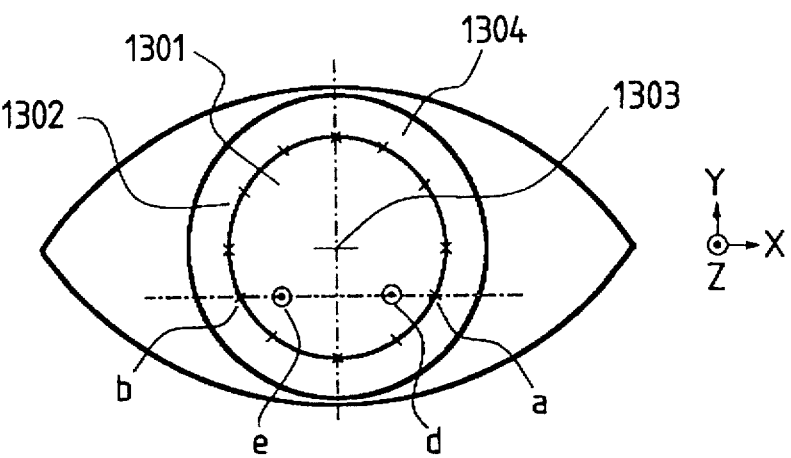
FIGS. 2A to 2C are views for explaining the principle of viewpoint detection.
Figure 2B:
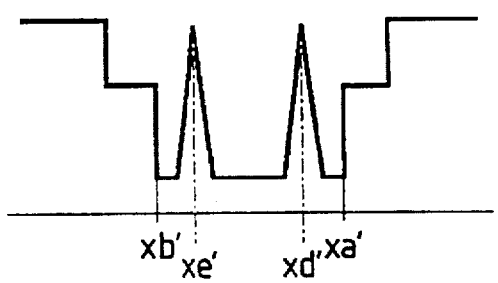
Figure 2C:
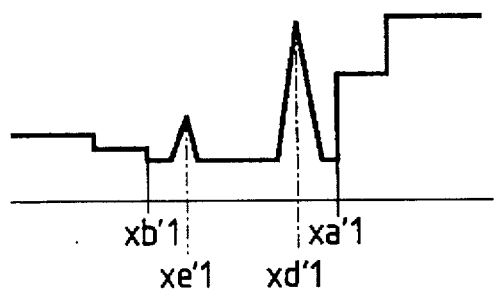
Figure 3:
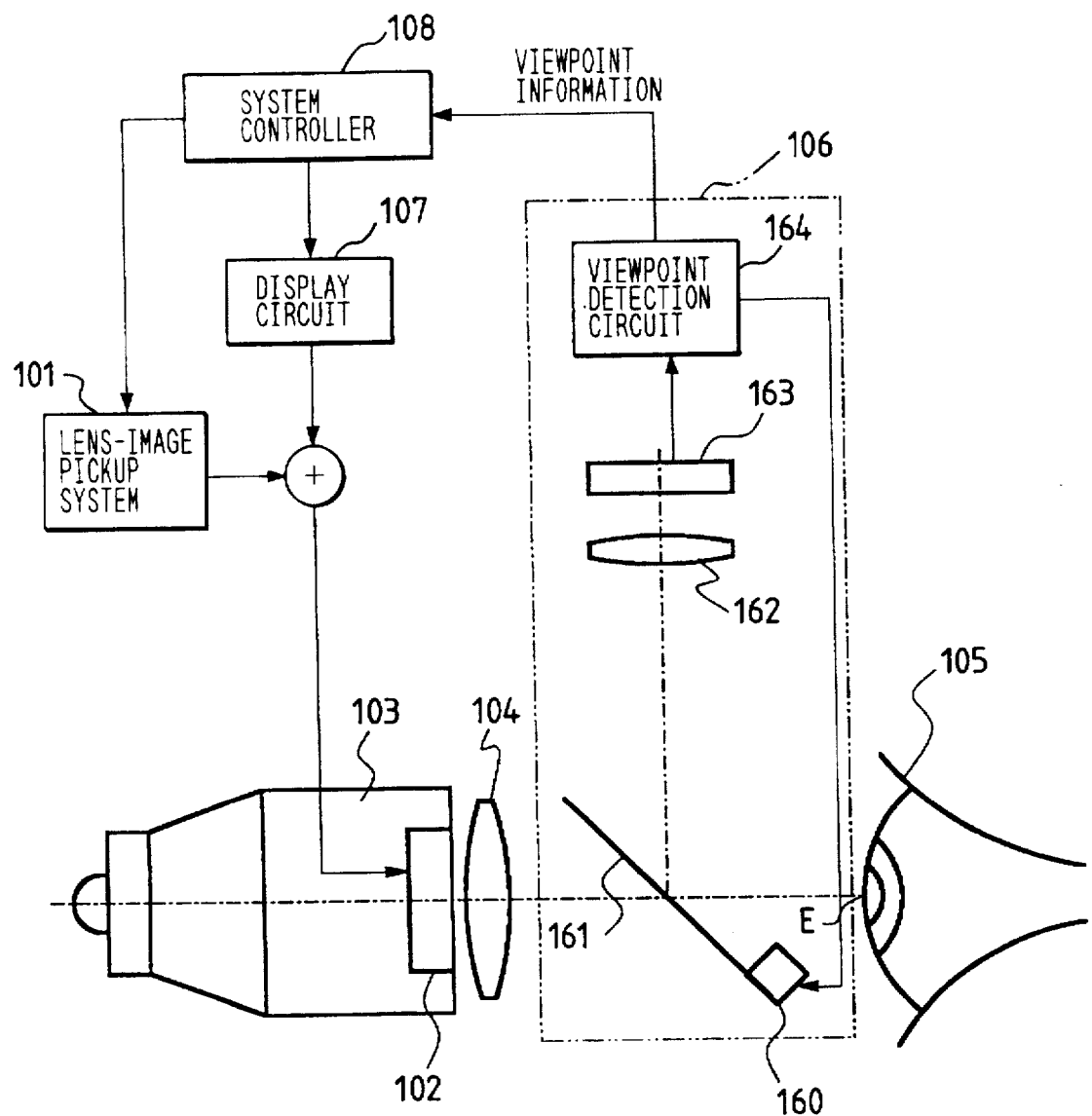
FIG. 3 is a block diagram showing the schematic arrangement of an image pickup apparatus with a viewpoint detection function.
Figure 6:
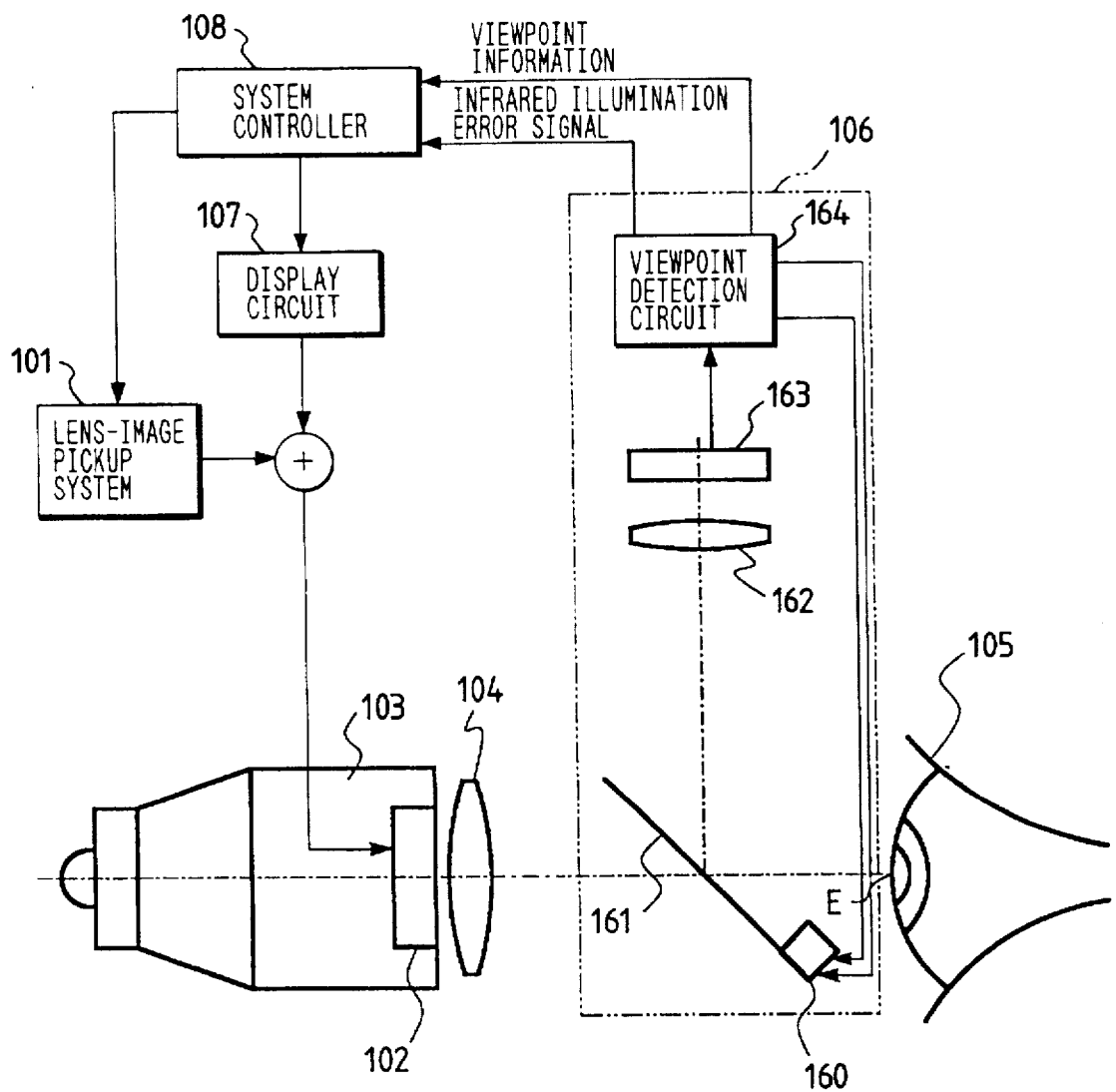
FIG. 6 is a block diagram showing the schematic arrangement of an image pickup apparatus with a viewpoint detection function according to an embodiment of the present invention.

FIG. 6 is a block diagram showing the schematic arrangement of an image pickup apparatus with a viewpoint detection function according to an embodiment of the present invention. Since the constituent elements of this apparatus are the same as those shown in FIG. 3, a description thereof will be omitted.

Figure 4:
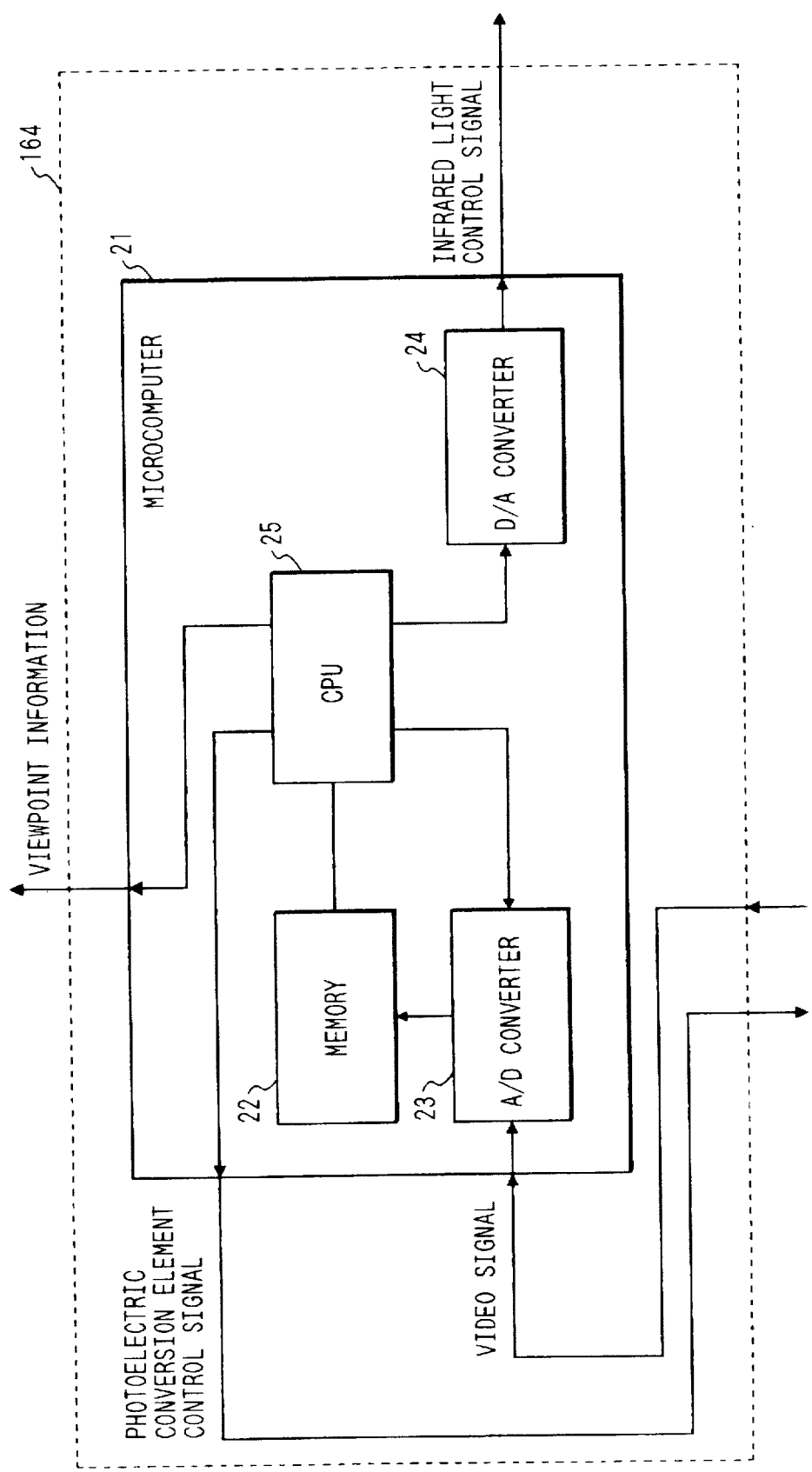
FIG. 4 is a block diagram showing the arrangement of a viewpoint detection circuit.
Figure 7:
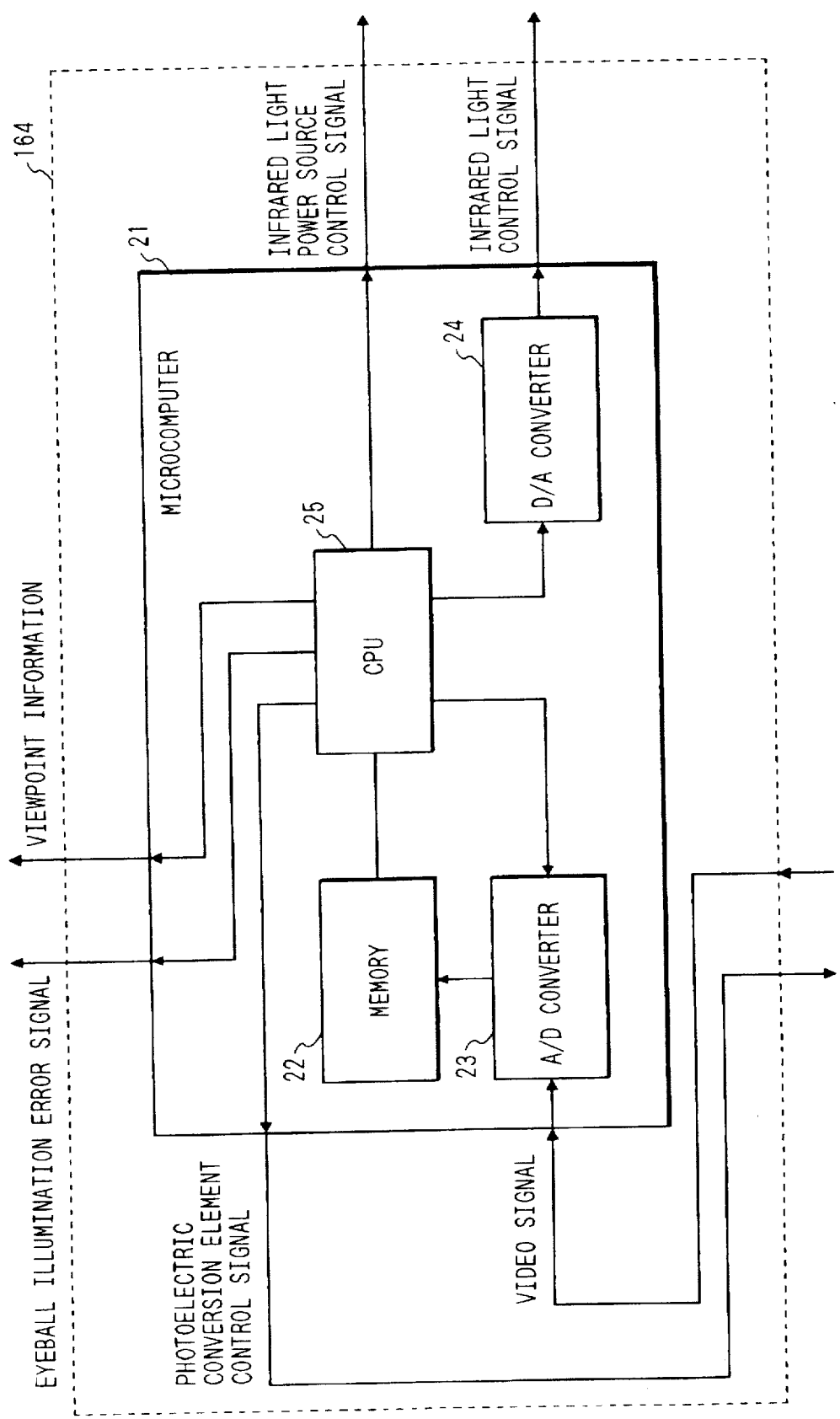
FIG. 7 is a block diagram showing the arrangement of a viewpoint detection circuit in the embodiment of the present invention.

FIG. 7 shows an example of the arrangement of a viewpoint detection circuit according to an embodiment of the present invention. Since the constituent elements of a viewpoint detection circuit 164 are the same as those shown in FIG. 4, only a different point will be briefly described. A microcomputer 21 is adapted to output an eyeball illumination error signal and an infrared light power source control signal in addition to conventional control signals.

Figure 8:
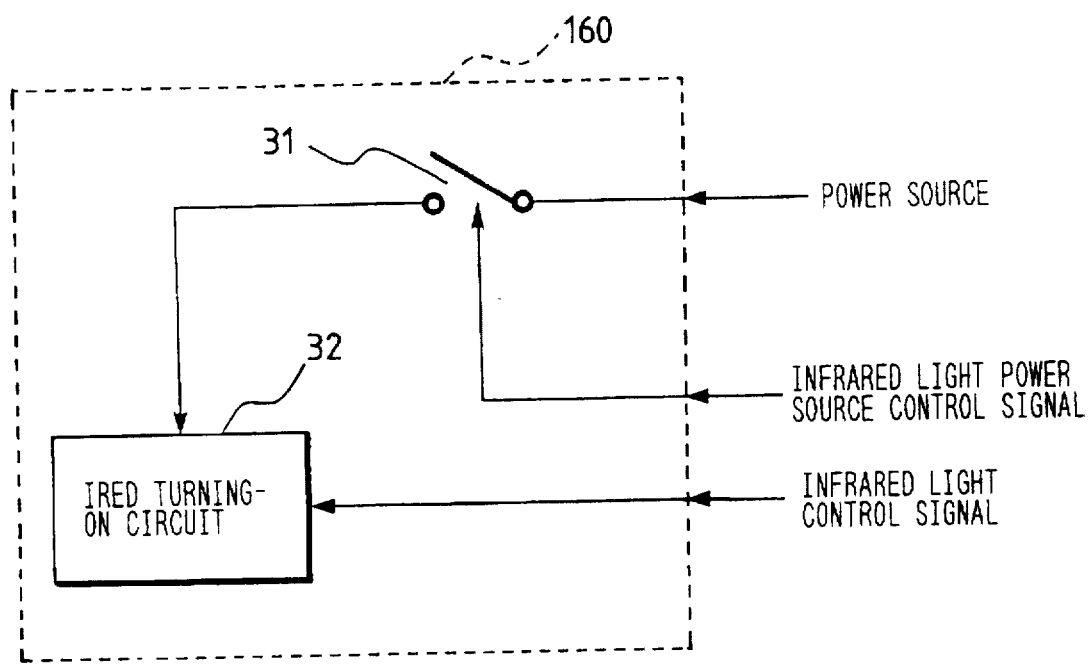
FIG. 8 is a block diagram showing the arrangement of an infrared light irradiation unit in the embodiment of the present invention.

FIG. 8 shows an example of the arrangement of an infrared light irradiation unit in this embodiment of the present invention. The infrared light irradiation unit includes a switch 31 and an IRED turning-on circuit 32. In this infrared light irradiation unit 160 (equivalent to the infrared-emitting diode in FIG. 6), external power supply (not shown) is input to the switch 31.

The IRED turning-on circuit 32 is constituted by an infrared-emitting diode (IRED), a transistor, and the like. Emission of the IRED is controlled by an infrared light control signal from the viewpoint detection circuit 164. The power supply of the IRED turning-on circuit 32 is connected to the switch 31. The switch 31 is opened/closed by an infrared light power source control signal from the viewpoint detection circuit 164.

Figure 9:
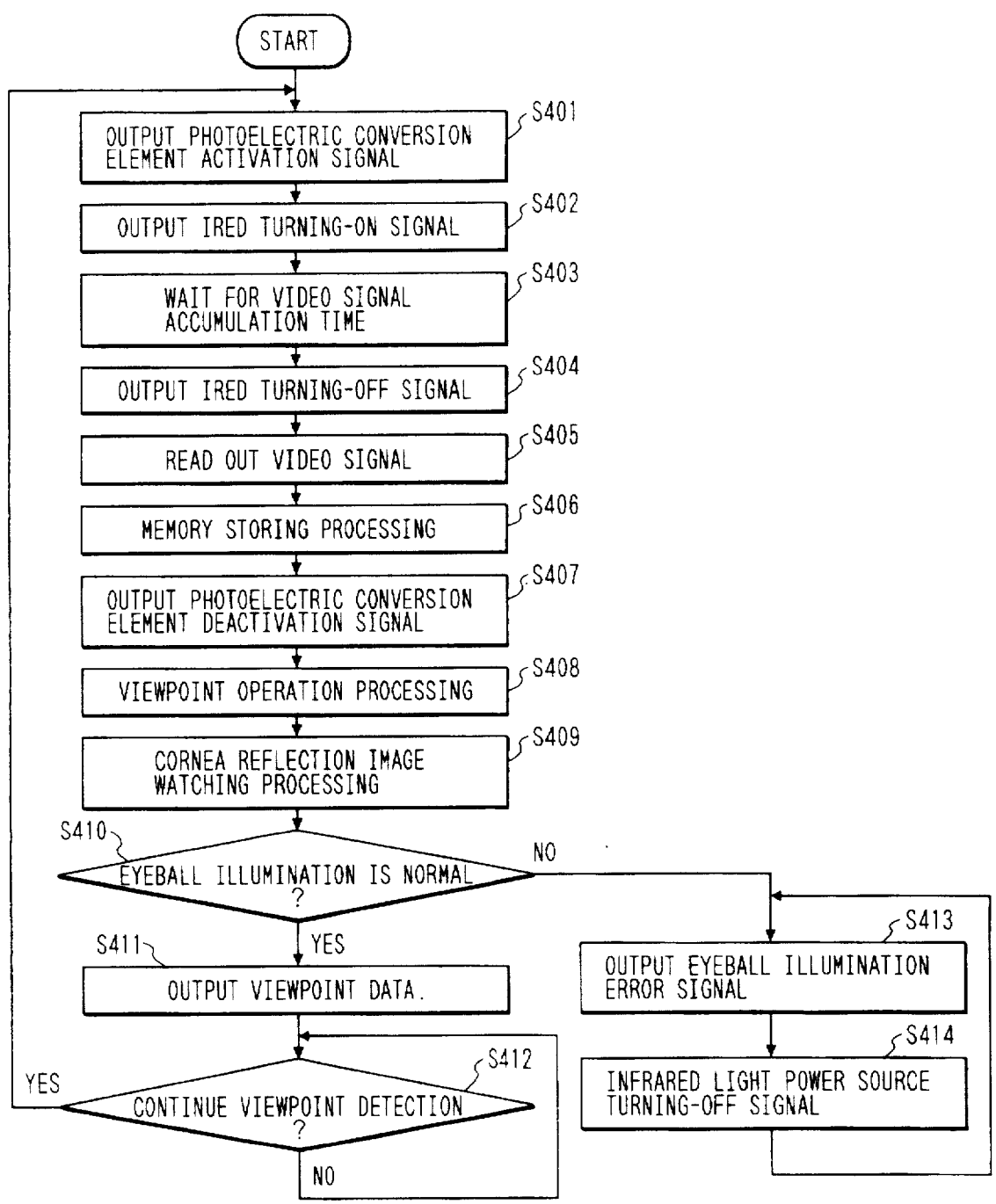
FIG. 9 is a flow chart showing viewpoint detection processing performed by the viewpoint detection circuit in the embodiment of the present invention.

FIG. 9 is a flow chart showing the flow of processing performed by the microcomputer 21 in the viewpoint detection circuit 164 in this embodiment of the present invention.

Figure 5:
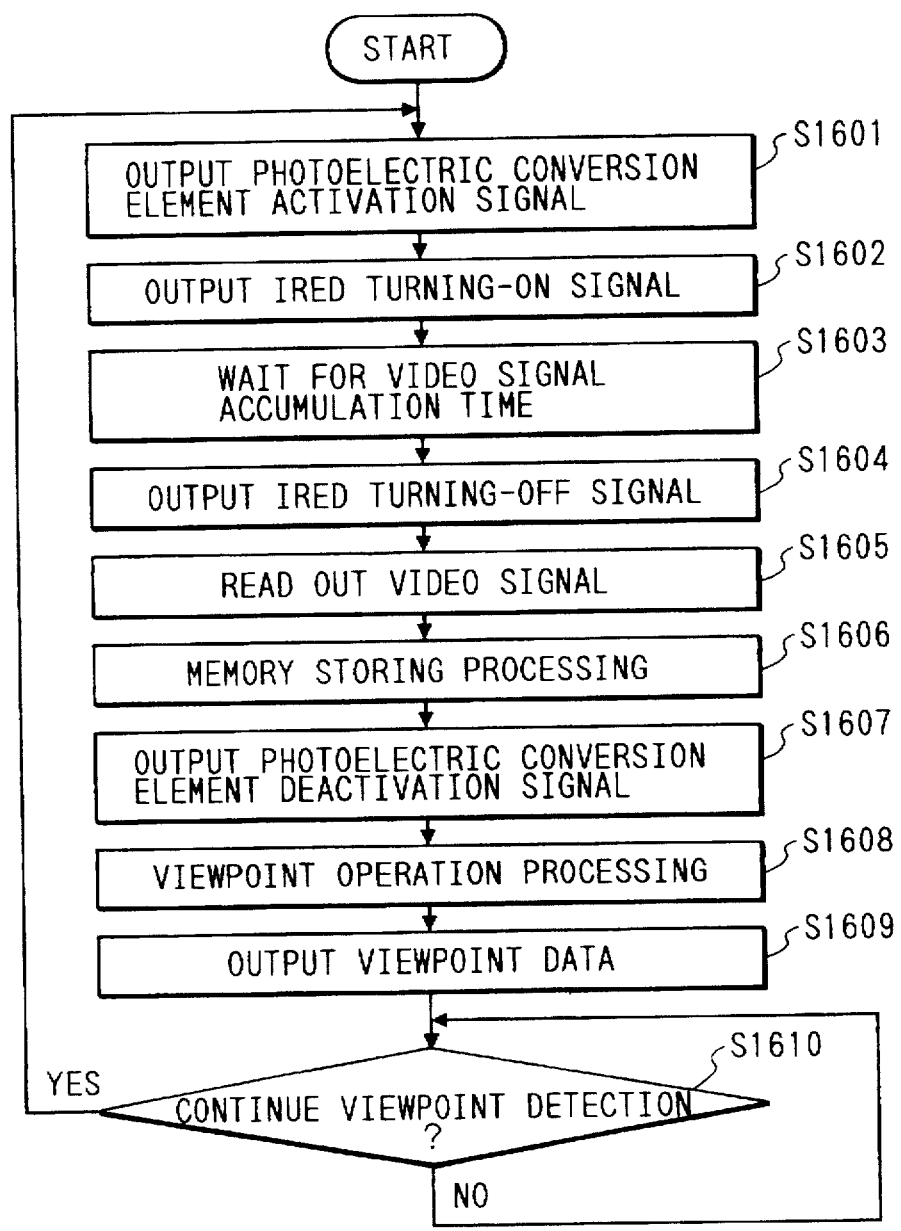
FIG. 5 is a flow chart showing viewpoint detection processing performed by the viewpoint detection circuit.

A CPU 25 of the microcomputer 21 performs the same processing as that in the arrangement shown in FIG. 5 from step S401 to step S408. That is, the CPU 25 outputs a photoelectric conversion element activation signal (step S401), and an IRED turning-on signal (step S402). The CPU 25 then waits until infrared light is irradiated on an eye 105 of a photographer and a reflection image is formed on a photoelectric conversion element 163 (step S403), and outputs an IRED turning-off signal (step S404).

The CPU 25 reads out a video signal representing the eye 105 of the photographer from the photoelectric conversion element 163 (step S405). The CPU 25 A/D-converts the signal with the A/D converter 23, and stores the resultant data in the internal memory 22 (step S406). The CPU 25 outputs a photoelectric conversion element deactivation signal (step S407), and obtains the viewpoint of the photographer on the viewfinder screen 102 by performing viewpoint operation processing on the basis of the video signal representing the eye 105 of the photographer which is stored in the internal memory 22 (step S408).

Subsequently, the CPU 25 performs predetermined cornea reflection image watching processing (step S409), and checks whether eyeball illumination is normally performed (step S410). If it is determined that eyeball illumination is normally performed, viewpoint data is output to the system controller 108 (step S411). The CPU 25 then checks whether to continue viewpoint detection (step S412). If it is determined that viewpoint detection is continued, the flow returns to step S401. Otherwise, the flow returns to step S412 to check again whether to continue viewpoint detection.

If it is determined that eyeball illumination is abnormally performed, the CPU 25 outputs an eyeball illumination error signal to the system controller 108 (step S413), and also outputs an infrared light power source turning-off signal to the infrared light irradiation unit 160 (step S414).

Figure 10:
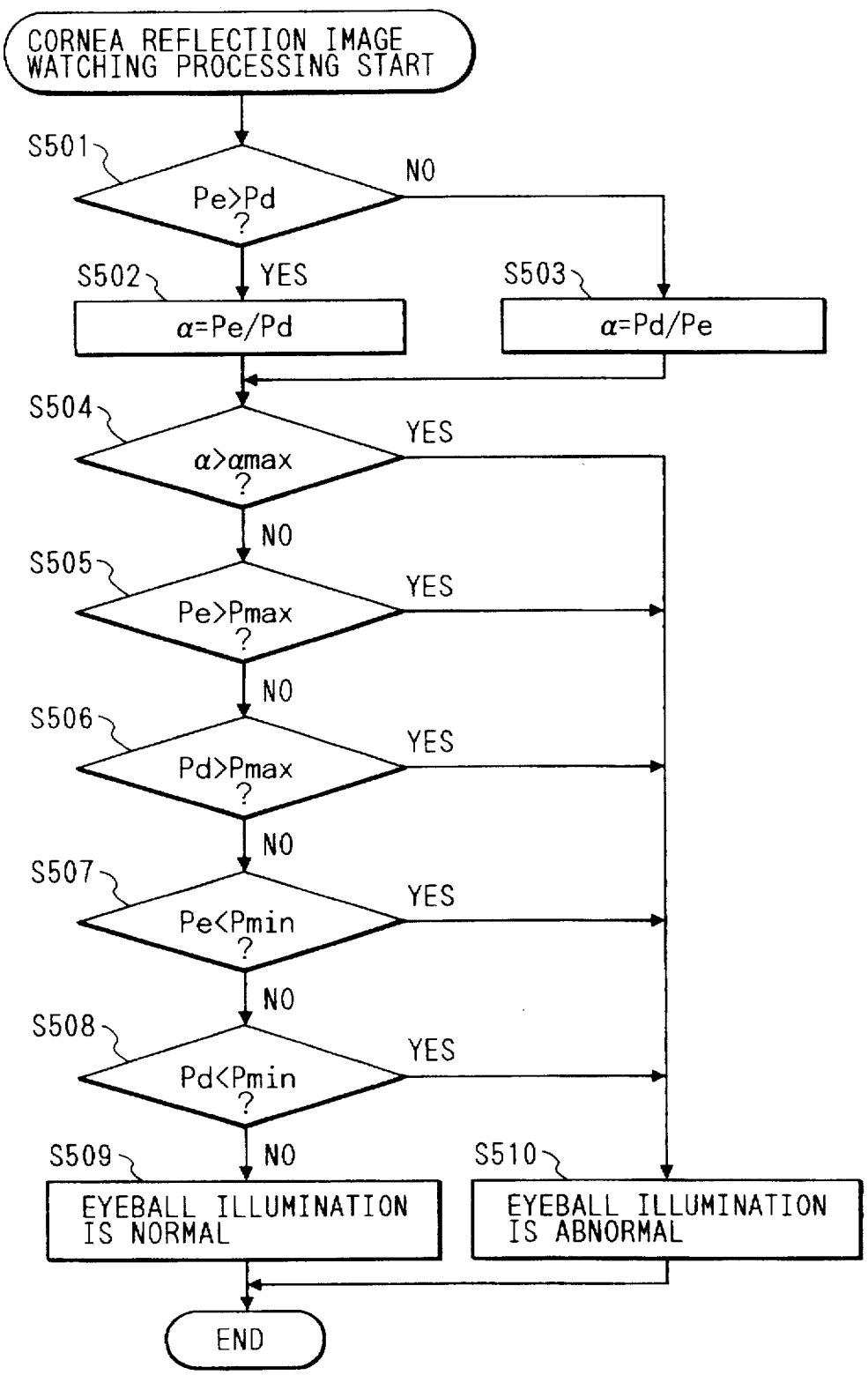
FIG. 10 is a flow chart showing cornea reflection image watching processing in the first embodiment of the present invention.

The first embodiment of the cornea reflection image watching processing in step S409 in FIG. 9 will be described next with reference to the flow chart of FIG. 10. Referring to FIG. 10, a level Pe is the image output level of a cornea reflection image e, and a level pd is the image output level of a cornea reflection image d.

In cornea reflection image watching processing, first of all, the image output levels (lightness, luminance) of the image output levels Pe and Pd of the cornea reflection images e and d are compared with each other, and a ratio $\alpha$ between the two image output levels is calculated (steps S501 to S503). The CPU 25 checks whether the ratio $\alpha$ between the image output levels is equal to or lower than a maximum allowable cornea reflection image ratio $\alpha$max (step S504). If $\alpha > \alpha$max, the CPU 25 determines abnormal eyeball illumination (step S510).

In addition, if the image levels Pe and Pd are higher than a maximum image output level Pmax (steps S505 and S506), or lower than a minimum image output level Pmin (steps S507 and S508), the CPU 25 determines abnormal eyeball illumination. If all these conditions are satisfied, the CPU 25 determines normal eyeball illumination (step S509).

Figure 12:
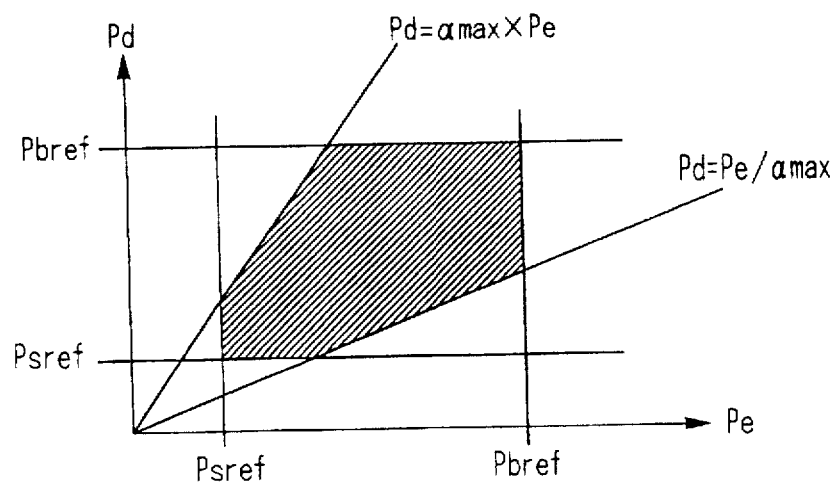
FIG. 12 is a graph showing the relationship between the output levels of two cornea reflection images in the first embodiment of the present invention.

FIG. 12 shows a state of the above determination. Referring to FIG. 12, the ordinate represents the image output level Pd of the cornea reflection image d; and the abscissa, the image output level Pe of the cornea reflection image e. In FIG. 12, when the image output levels Pd and Pe have a relationship corresponding to the hatched portion, it is determined that eyeball illumination is normal. Otherwise, an eyeball illumination error is determined.

Figure 11A:
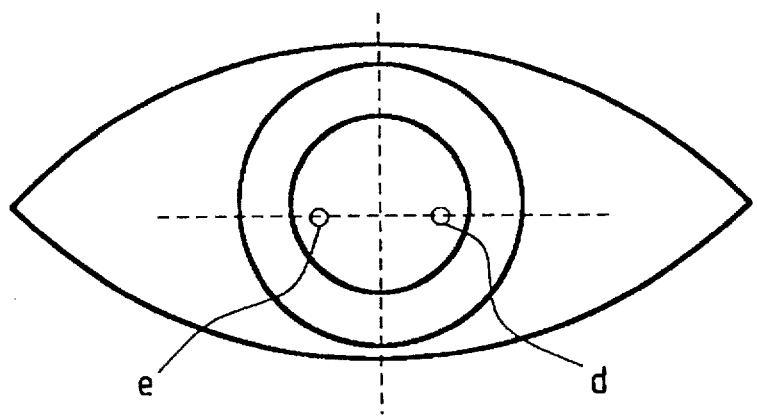
FIGS. 11A to 11D are views showing output signals representing cornea reflection images.
Figure 11B:
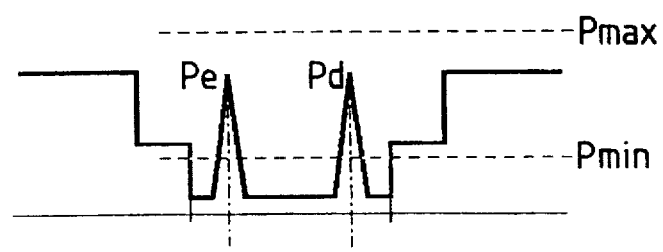
Figure 11C:
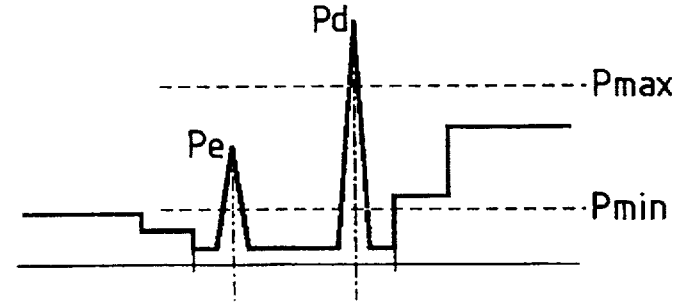
Figure 11D:
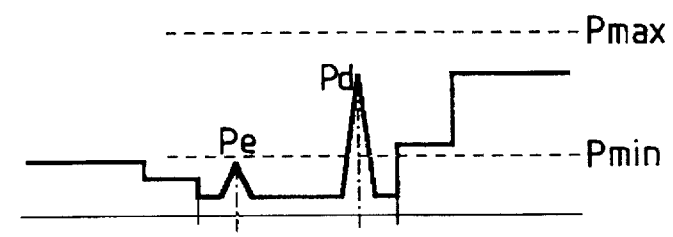
Figure 13A:
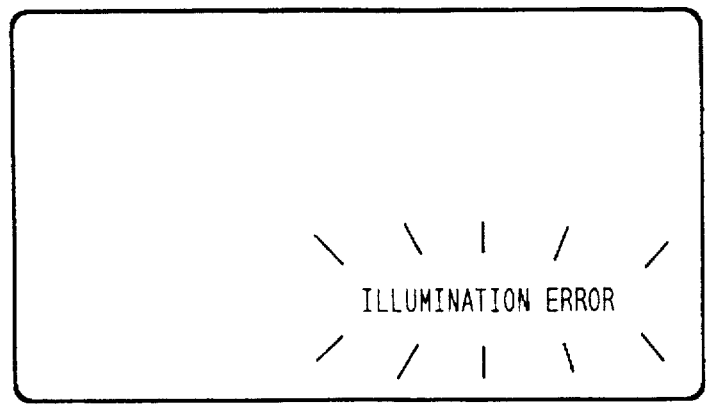
FIGS. 13A and 13B are views showing examples of how eyeball illumination errors are warned.

With this processing, in the case of the cornea reflection image shown in FIG. 11B, it is determined that eyeball illumination is normal. In the cases of the cornea reflection images shown in FIGS. 11C and 11D, it is determined that eyeball illumination is abnormal. If abnormal eyeball illumination is determined, an eyeball illumination error signal is output to a system controller 108 in FIG. 6. The system controller 108 controls a display circuit 107 to perform eyeball illumination error display. As a result, the display circuit 107 performs eyeball illumination error display like the one shown in FIG. 13A on a viewfinder screen 102, thereby warning the photographer.

Figure 13B:
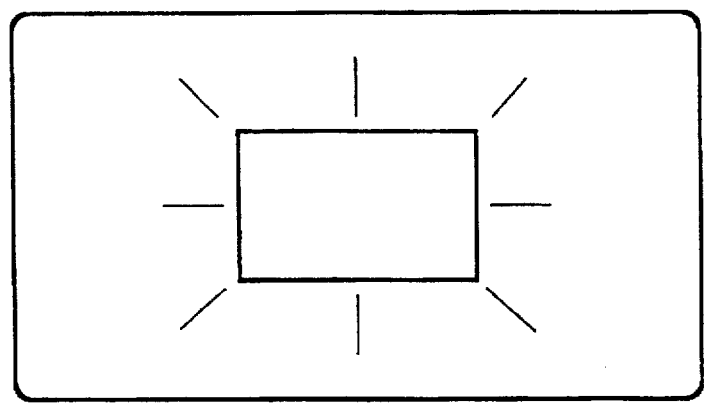

A warning need not be given through a message in characters but may be given by changing a turn-on display of the AF frame in a normal state to a flickering display, as shown in FIG. 13B. If one of the image output levels Pe and Pd is higher than the maximum image output level Pmax or less than the minimum image output level Pmin, a warning is given indicating that an abnormality has occurred in a corresponding light-emitting diode 1206a or 1206b. In this manner, a warning is given by individually indicating a light-emitting diode in which the abnormality has occurred, thereby allowing more accurate maintenance.

If an eyeball illumination error is determined, the viewpoint detection circuit 164 in FIG. 6 outputs an infrared light power source turning-off signal to the infrared light irradiation unit 160. With this operation, the switch 31 is turned off to turn off the power supply of the IRED turning-on circuit 32. Therefore, unnecessary power consumption can be suppressed. In addition, the operation prevents unintentional execution of the zooming function, the fading function, or the like when a viewpoint switch other than a desired one is turned on, or prevents the camera from being focused on an object other than an object to be photographed.

Figure 14:
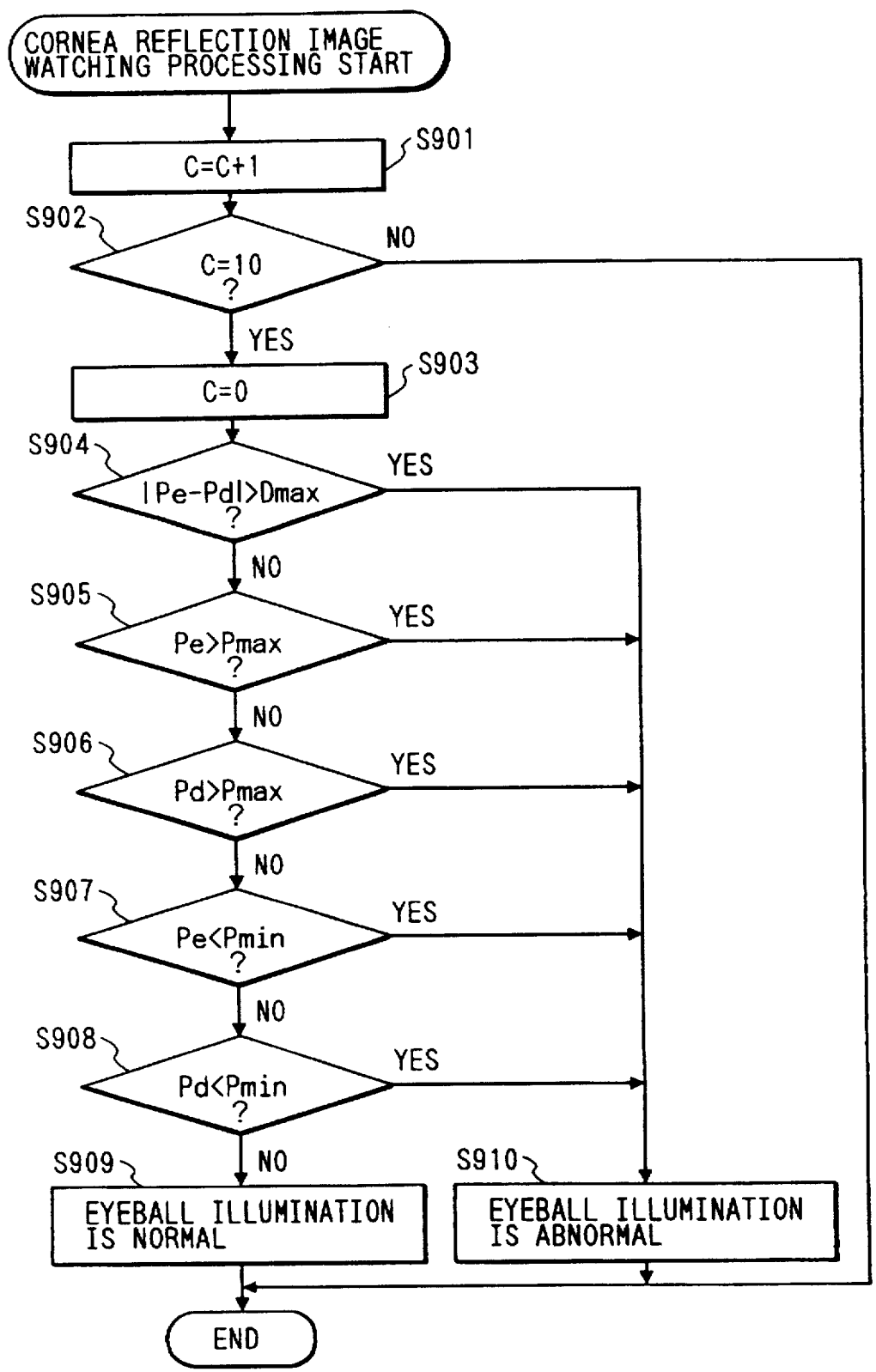
FIG. 14 is a flow chart showing cornea reflection image watching processing in the second embodiment of the present invention.

Cornea reflection image watching processing in the second embodiment will be described next with reference to the flow chart of FIG. 14.

In the second embodiment, eyeball illumination abnormality determination is not performed for each viewpoint detection processing but is performed once for every 10 viewpoint detection processing operations.

More specifically, a viewpoint detection processing counter C is incremented by "1" (step S901), and it is checked whether the viewpoint detection processing count in the viewpoint detection processing counter C is "10" (step S902). If the viewpoint detection processing count is not "10", the processing is immediately terminated, thereby avoiding eyeball illumination abnormality determination processing.

If the viewpoint detection processing count is "10", the viewpoint detection processing counter C is reset to "0" (step S904). Thereafter, eyeball illumination abnormality determination is performed according to almost the same conditions as those in the first embodiment shown in FIG. 10 (steps S904 to S910), and hence a detailed description thereof will be omitted. However, this embodiment is different from the first embodiment in that an absolute value D of the difference between two image output levels is used as a determination criterion instead of the ratio $\alpha$ between two image output levels, and an eyeball illumination abnormality is determined on the condition that the absolute value D of the difference is larger than a maximum allowable value Dmax.

Figure 15:
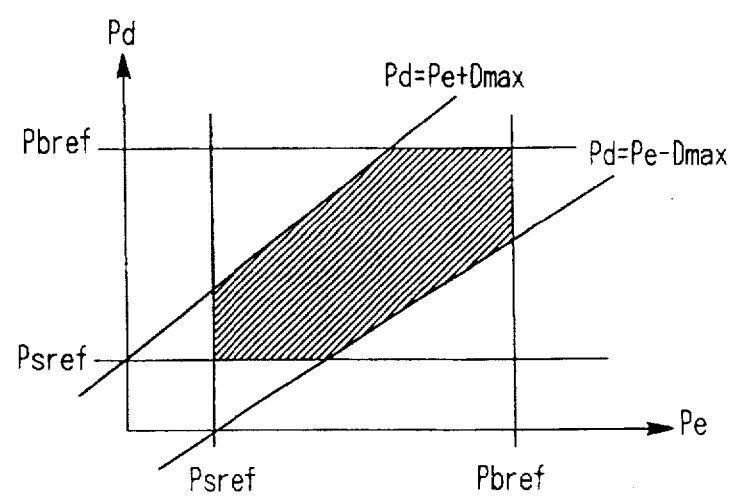
FIG. 15 is a graph showing the relationship between the output levels of two cornea reflection images in the second embodiment of the present invention.

In this embodiment, the image output levels Pe and Pd of the cornea reflection images e and d by which normal eyeball illumination is determined as a result of the above processing have a relationship corresponding to the hatched portion shown in FIG. 15. In the embodiment, the time required for cornea reflection image watching processing is short relative to the time required for viewpoint detection processing. Therefore, in continuous viewpoint detection processing, the number of times of viewpoint detection per unit time can be decreased.

In this embodiment, eyeball illumination abnormality determination can be performed under the same conditions as those in the first embodiment. In addition, the intervals at which eyeball illumination abnormality determination is performed may not be "once for every ten viewpoint detection processing operations", but may be arbitrarily set. Furthermore, the intervals may be changed in accordance with the state of an eye of the photographer.

Figure 16:
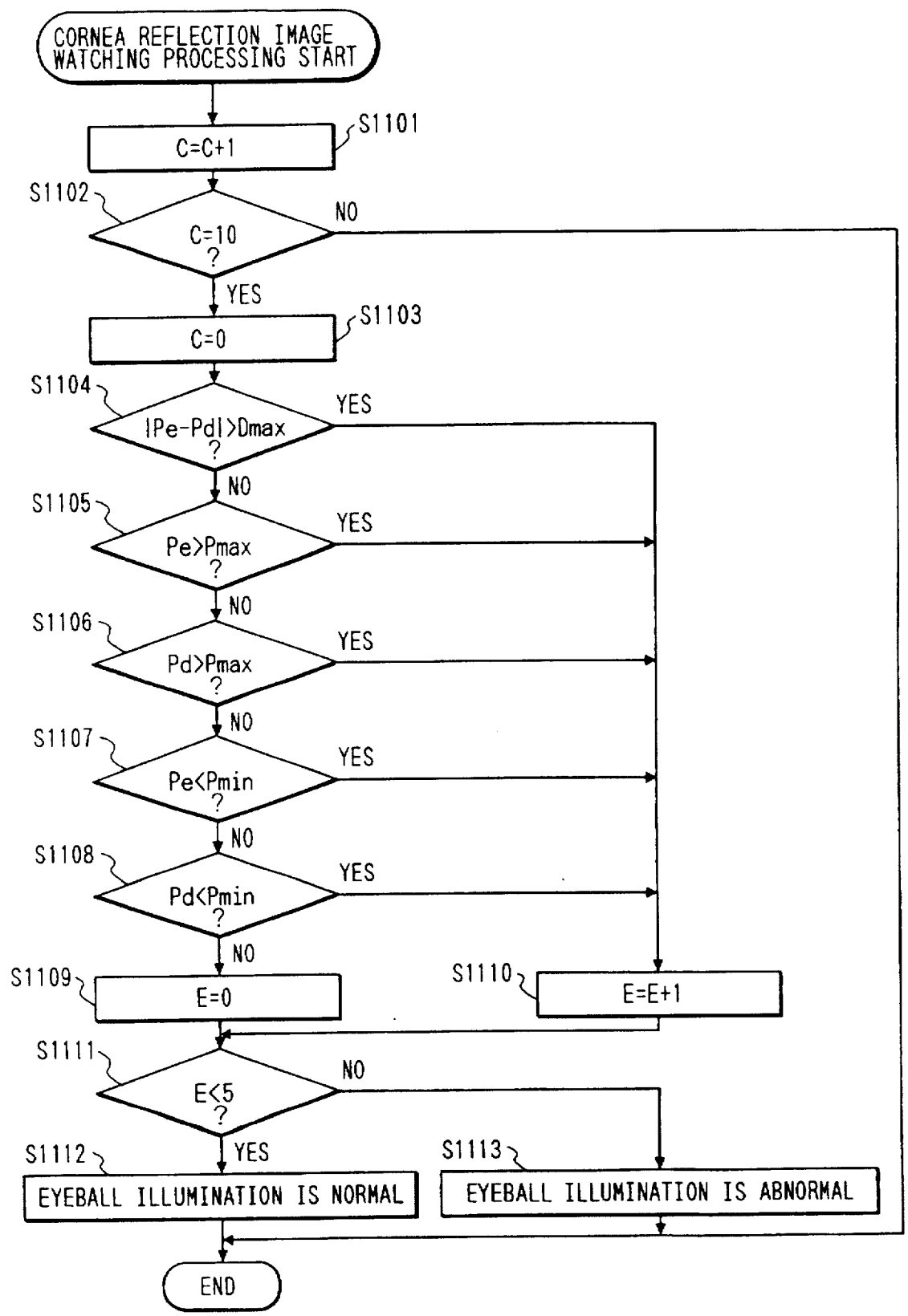
FIG. 16 is a flow chart showing the flow of cornea reflection image watching processing in the third embodiment of the present invention.

Cornea reflection image watching processing in the third embodiment will be described next with reference to the flow chart of FIG. 16.

In the third embodiment, eyeball illumination abnormality determination is performed once for every 10 viewpoint detection processing operations. However, with the addition of steps S1109, S1110, and S1111, abnormal eyeball illumination is determined when the determination condition is satisfied five times consecutively, unlike in the first and second embodiments, in which abnormal eyeball illumination is determined when the determination condition is satisfied once.

More specifically, when the determination condition is satisfied once, a determination condition satisfaction counter E is incremented by "1" (step S1110), and it is checked whether the determination condition satisfaction count has reached "5" (step S1111). If it is determined that the determination condition satisfaction count has reached "5", abnormal eyeball illumination is determined (step S1113). If the determination condition satisfaction count has not reached "5", normal eyeball illumination is determined (step S1112).

If the determination condition is satisfied five times, the determination condition satisfaction counter E is cleared to "0" (step S1109). When the determination condition is satisfied five times consecutively, it is determined that eyeball illumination is abnormal.

With this processing, abnormal eyeball illumination is not immediately determined with an instantaneous change in a cornea reflection image due to tears or the like in the eye. Therefore, a change in a cornea reflection image due to abnormal eyeball illumination can be more accurately checked. In this embodiment, abnormal eyeball illumination is determined when the determination condition is satisfied five times consecutively. As is apparent, however, the threshold value of this count need not be five, but may be arbitrarily set.

The present invention is not limited to the above embodiments. For example, the present invention can be applied to a case wherein only one eyeball illumination means (light source) such as an infrared-emitting diode is arranged, instead of a plurality of eyeball illumination means.

As described above, according to the embodiments of the present invention, since an abnormality in the eyeball illumination means is determined on the basis of the lightness of each cornea reflection image, an abnormality in the eyeball illumination means can be automatically determined in viewpoint detection, thereby effectively preventing operation errors and unnecessary power consumption.

In addition, the abnormality determination means determines an abnormality in the eyeball illumination means on the basis of the lightness of each cornea reflection image detected by the lightness detection means. When an abnormality is determined, power supply to the eyeball illumination means is stopped by the power supply stopping means. Therefore, an abnormality in the eyeball illumination means can be automatically determined in a viewpoint detecting operation, and proper measures such as a power off operation can be automatically executed.

According to the above embodiments, the abnormality determination means determines an abnormality in the eyeball illumination means on the basis of the lightness of each cornea reflection image detected by the lightness detection means. When the abnormality determination means determines that the eyeball illumination means is abnormal, the warning means gives a corresponding warning. With this operation, an abnormality in the eyeball illumination means can be automatically determined in a viewpoint detecting operation, and proper measures can be quickly taken.

In addition, the lightness detection means detects the lightness of each cornea reflection image at a plurality of positions. With this operation, an abnormality in the eyeball illumination means can be automatically determined more accurately in a viewpoint detecting operation, or more proper measures can be taken.

According to the above embodiments, the abnormality determination means determines an abnormality in the eyeball illumination means by comparing the ratio between the lightnesses of each cornea reflection image at a plurality of positions, which are detected by the lightness detection means, with a reference value, thereby automatically determining an abnormality in the eyeball illumination means more accurately in a viewpoint detecting operation, or taking more proper measures.

In addition, according to the above embodiments, the abnormality determination means determines an abnormality in the eyeball illumination means by comparing the difference between the lightnesses of each cornea reflection image at a plurality of positions, which are detected by the lightness detection means, with a reference value, thereby automatically determining an abnormality in the eyeball illumination means more accurately in a viewpoint detecting operation, or taking more proper measures.

Furthermore, according to the above embodiments, determination of any abnormality in the eyeball illumination means is performed every time viewpoint detection processing is performed a plurality of number of times by the viewpoint detection means. With this operation, an abnormality in the eyeball illumination means can be automatically determined in a viewpoint detecting operation, or more proper measures can be taken. In addition, by increasing the viewpoint detection processing count per unit time, high-precision determination can be realized.

The abnormality determination means determines an abnormality in the eyeball illumination means when a predetermined determination condition is consecutively satisfied while viewpoint detection processing is performed by the viewpoint detection means a plurality of number of times. With this operation, an abnormality in the eyeball illumination means can be automatically determined, or more proper measures can be taken. In addition, the operation can prevent erroneous determination of an abnormality in the eyeball illumination means when an instantaneous change in the lightness of each cornea reflection image is caused by tears or the like. Therefore, more reliable detection and determination can be performed.

As has been described above, an abnormality in the eyeball illumination means is automatically determined in a viewpoint detecting operation, and the power supply of the eyeball illumination means is turned off in accordance with the determination, or a warning is generated, thereby improving maintainability and suppressing unnecessary power consumption. Also, this operation prevents unintentional execution of the zooming function, the fading function, or the like when a viewpoint switch other than a desired one is turned on, or prevents the camera from being focused on an object other than an object to be photographed.

What is claimed is:

1. A viewpoint detection apparatus comprising:
   A) eyeball illumination means for illuminating an eyeball;
   B) viewpoint detection means for detecting a viewpoint on the basis of a cornea reflection image corresponding to light irradiated on the eyeball by said eyeball illumination means;
   C) lightness detection means for detecting a lightness of the cornea reflection image; and
   D) abnormality determination means for determining that said eyeball illumination means works abnormally, on the basis of the lightness of the cornea reflection image detected by said lightness detection means.

2. An apparatus according to claim 1, wherein said eyeball illumination means has an infrared-emitting diode (IRED) and illuminates the eyeball with infrared light.

3. An apparatus according to claim 1, wherein said viewpoint detection means includes a CCD for imaging a cornea reflection image, and said lightness detection means detects the lightness of the cornea reflection image at a plurality of positions.

4. An apparatus according to claim 1, wherein said abnormality determination means determines an abnormality in said eyeball illumination means by comparing a ratio between lightnesses of the cornea reflection image at a plurality of positions, which are detected by said lightness detection means, with a reference value.

5. An apparatus according to claim 1, wherein said abnormality determination means determines an abnormality in said eyeball illumination means by comparing a difference between lightnesses of the cornea reflection image at a plurality of positions, which are detected by said lightness detection means, with a reference value.

6. An apparatus according to claim 1, wherein said abnormality determination means determines an abnormality in said eyeball illumination means by comparing lightnesses of the cornea reflection image at a plurality of positions, which are detected by said lightness detection means, with a reference value.

7. An apparatus according to claim 1, wherein said abnormality determination means determines an abnormality in said eyeball illumination means every time viewpoint detection processing is performed by said viewpoint detection means a plurality of number of times.

8. An apparatus according to claim 7, wherein said abnormality determination means determines that said eyeball illumination means is abnormal, when a predetermined determination condition is satisfied not less than a predetermined number of times in a plurality of number of times of viewpoint detection processing performed by said viewpoint detection means.

9. An apparatus according to claim 8, wherein said abnormality determination means determines that said eyeball illumination means is abnormal, when the predetermined determination condition is satisfied the predetermined number of times consecutively in a plurality of number of times of viewpoint detection processing performed by said viewpoint detection means.

10. A viewpoint detection apparatus comprising:
    A) eyeball illumination means for illuminating an eyeball;
    B) viewpoint detection means for detecting a viewpoint on the basis of a cornea reflection image corresponding to light irradiated on the eyeball by said eyeball illumination means;
    C) lightness detection means for detecting a lightness of the cornea reflection image;
    D) abnormality determination means for determining that said eyeball illumination means works abnormally, on the basis of the lightness of the cornea reflection image detected by said lightness detection means; and
    E) power supply stopping means for stopping power supply to said eyeball illumination means when said abnormality determination means determines that said eyeball illumination means is abnormal.

11. An apparatus according to claim 10, wherein said eyeball illumination means has an infrared-emitting diode (IRED), said viewpoint detection means includes a CCD for imaging a cornea reflection image, and said lightness detection means detects the lightness of the cornea reflection image at a plurality of positions.

12. An apparatus according to claim 10, wherein said abnormality determination means determines an abnormality in said eyeball illumination means by comparing a ratio between lightnesses of the cornea reflection image at a plurality of positions, which are detected by said lightness detection means, with a reference value.

13. An apparatus according to claim 10, wherein said abnormality determination means determines an abnormality in said eyeball illumination means by comparing a difference between lightnesses of the cornea reflection image at a plurality of positions, which are detected by said lightness detection means, with a reference value.

14. An apparatus according to claim 10, wherein said abnormality determination means determines an abnormality in said eyeball illumination means by comparing lightnesses of the cornea reflection image at a plurality of positions, which are detected by said lightness detection means, with a reference value.

15. An apparatus according to claim 10, wherein said abnormality determination means determines an abnormality in said eyeball illumination means every time viewpoint detection processing is performed by said viewpoint detection means a plurality of number of times.

16. An apparatus according to claim 10, wherein said abnormality determination means determines that said eyeball illumination means is abnormal, when the predetermined determination condition is satisfied the predetermined number of times consecutively in a plurality of number of times of viewpoint detection processing performed by said viewpoint detection means.

17. A viewpoint detection apparatus comprising:
    A) eyeball illumination means for illuminating an eyeball;
    B) viewpoint detection means for detecting a viewpoint on the basis of a cornea reflection image corresponding to light irradiated on the eyeball by said eyeball illumination means;
    C) lightness detection means for detecting a lightness of the cornea reflection image;
    D) abnormality determination means for determining that said eyeball illumination means works abnormally, on the basis of the lightness of the cornea reflection image detected by said lightness detection means; and
    E) warning means for warning of an abnormality when said abnormality determination means determines that said eyeball illumination means is abnormal.

18. An apparatus according to claim 17, further comprising power supply stopping means for stopping power supply to said eyeball illumination means when said abnormality determination means determines that said eyeball illumination means is abnormal.

19. An apparatus according to claim 17, wherein said eyeball illumination means has an infrared-emitting diode (IRED), said viewpoint detection means includes a CCD for imaging a cornea reflection image, and said lightness detection means detects the lightness of the cornea reflection image at a plurality of positions.

20. An apparatus according to claim 19, wherein said abnormality determination means determines an abnormality in said eyeball illumination means by comparing a ratio between lightnesses of the cornea reflection image at a plurality of positions, which are detected by said lightness detection means, with a reference value.

21. An apparatus according to claim 19, wherein said abnormality determination means determines an abnormality in said eyeball illumination means by comparing a difference between lightnesses of the cornea reflection image at a plurality of positions, which are detected by said lightness detection means, with a reference value.

22. An apparatus according to claim 19, wherein said abnormality determination means determines an abnormality in said eyeball illumination means by comparing lightnesses of the cornea reflection image at a plurality of positions, which are detected by said lightness detection means, with a reference value.

23. An apparatus according to claim 19, wherein said abnormality determination means determines an abnormality in said eyeball illumination means every time viewpoint detection processing is performed by said viewpoint detection means a plurality of number of times.

24. An apparatus according to claim 19, wherein said abnormality determination means determines that said eyeball illumination means is abnormal, when the predetermined determination condition is satisfied the predetermined number of times consecutively in a plurality of number of times of viewpoint detection processing performed by said viewpoint detection means.

25. A video camera having a viewpoint detection apparatus, comprising:

A) an electronic viewfinder;

B) eyeball illumination means for illuminating an eyeball corresponding to a viewpoint on a screen of said electronic viewfinder;

C) viewpoint detection means for detecting a viewpoint on the basis of a cornea reflection image corresponding to light irradiated on the eyeball by said eyeball illumination means;

D) lightness detection means for detecting a lightness of the cornea reflection image;

E) abnormality determination means for determining that said eyeball illumination means works abnormally, on the basis of the lightness of the cornea reflection image detected by said lightness detection means; and F) warning means for displaying a warning of an abnormality on the screen of said electronic viewfinder when said abnormality determination means determines that said eyeball illumination means is abnormal.

26. A camera according to claim 25, further comprising power supply stopping means for stopping power supply to said eyeball illumination means when said abnormality determination means determines that said eyeball illumination means is abnormal.

27. A camera according to claim 25, wherein said abnormality determination means determines an abnormality in said eyeball illumination means by comparing a ratio between lightnesses of the cornea reflection image at a plurality of positions, which are detected by said lightness detection means, with a reference value.

28. A camera according to claim 25, wherein said abnormality determination means determines an abnormality in said eyeball illumination means by comparing a difference between lightnesses of the cornea reflection image at a plurality of positions, which are detected by said lightness detection means, with a reference value.

29. A camera according to claim 25, wherein said abnormality determination means determines an abnormality in said eyeball illumination means by comparing lightnesses of the cornea reflection image at a plurality of positions, which are detected by said lightness detection means, with a reference value.

30. A camera according to claim 25, wherein said abnormality determination means determines that said eyeball illumination means is abnormal, when the predetermined determination condition is satisfied the predetermined number of times consecutively in a plurality of number of times of viewpoint detection processing performed by said viewpoint detection means.

* * * * *

UNITED STATES PATENT AND TRADEMARK OFFICE
CERTIFICATE OF CORRECTION

PATENT NO. : 5,757,428
DATED : May 26, 1998
INVENTOR(S) : HIROFUMI TAKEI

It is certified that error appears in the above-identified patent and that said Letters Patent is hereby corrected as shown below:

On the title page,
At [56] References Cited

"1234511" should read --1-241511--.

COLUMN 1

Line 26, "distance" should read --a distance--.

Column 7

Line 55, "If" should read --if--.

Signed and Sealed this

Second Day of February, 1999

Attest:

Attesting Officer

Acting Commissioner of Patents and Trademarks